United States Patent [19]

Palladino

[11] Patent Number: 4,683,199
[45] Date of Patent: Jul. 28, 1987

[54] INTERLEUKIN-2 DEPENDENT CYTOTOXIC T-CELL CLONES

[75] Inventor: Michael Palladino, New York, N.Y.

[73] Assignee: Sloan-Kettering Institute for Cancer Research, New York, N.Y.

[21] Appl. No.: 462,268

[22] Filed: Jan. 31, 1983

[51] Int. Cl.$^4$ .................... C12P 21/00; C12N 15/00; C12N 5/00; C12R 1/91

[52] U.S. Cl. .................................. 435/68; 435/172.2; 435/240; 435/948; 530/351; 530/828; 514/2; 514/8; 514/12

[58] Field of Search .................... 435/68, 172.2, 172.3, 435/240, 244, 948

[56] References Cited

U.S. PATENT DOCUMENTS 4,285,929  8/1981  Sugimoto et al. .................... 435/68

OTHER PUBLICATIONS

Wiranowska-Stewart et al, *J. Interferon Res.*, vol. 1 (2), 1981, "Determination of Human Leukocyte Population Involved in Production of Interferons Alpha and Gamma".

Farrar et al, from *Lymphokines*, vol. 5, Editor Edgar Pick, 1982, Academic Press, pp. 355–358.

Marcucci et al. "Production of Immune Interferon by Murine T cell Clones from Long Term Cultures" Nature vol. 291, pp. 79–81, May 7, 1981.

Klein et al, "Cytotoxic T Lymphocytes Produce Immune Interferon in Response to Antigen or Mitogen", J. Exp. Med., vol. 155, pp. 1198–1203, Apr. 1982.

McKimm-Breschkin et al, "Antigen-Specific Production of Immune Interferon by T cell Kinesires", J. Exp. Med. vol. 155, pp. 1204–1209, Apr. 1982.

DeLeo et al, "Cell Surface Antigens of Chemically Induced Sarcomas of the Mouse", J. Exp. Med. vol. 146, pp. 720–734, 1977.

Braciale et al; "Heterogeneity and Specificity of Cloned Lines of Influenza-Virus-Specificytotoxic T Lymphocytes", J. Exp. Med. vol. 153, pp. 910–923, Apr. 1981.

Duprez, et al; "Cell-Mediated Anti-Tumor Response in the RL δ 1 System" European J. Immunology, vol. 8, pp. 650–655, Sep. 1978.

Nakayama, et al, "Definition of a Unique Cell Surface Antigen of Mouse Leukemia RL δ 1 by Cell Mediated Cytotoxicity", Proc. Natl. Acad. Sci, vol. 76, No. 7, pp. 3486–3490, Jul. 1979.

Gillis et al, "Long Term Culture of Tumor-Specific Cytotoxic T Cells", Nature vol. 268, pp. 154–156, Jul. 14, 1977.

*Primary Examiner*—Thomas G. Wiseman
*Assistant Examiner*—Robin Lyn Teskin
*Attorney, Agent, or Firm*—John P. White

[57] ABSTRACT

Interleukin-2 dependent cytotoxic cultured T-cell lines are found to produce α, β, and γ interferon, as well as interleukin-2, when stimulated by mitogenic or antigenic agents.

9 Claims, No Drawings

INTERLEUKIN-2 DEPENDENT CYTOTOXIC T-CELL CLONES

This present invention was wholly or partially made with funds provided by the Department of Human Health and Services under Grant No. NIH-AM 00589. Accordingly, the United States Government has certain rights in this invention.

BACKGROUND OF THE INVENTION

T-cells are the principal cells of the mammalian immunological system. They are produced in the thymus from stem cells of bone marrow. T-cells are responsible for maintaining tissue integrity and cell-mediated immunity. It is known that the in vivo mechanism of T-cell action comprises activation of surface receptor sites on T-cells: upon contact with foreign antigens such as invading bacteria or foreign cells, which causes the T-cells to transform into blast cells and to release mediator chemicals called lymphokines which induce various immunological responses including the production of interferon (IFN).

Further advances in the understanding of T-cell function and lymphokines have awaited in vitro culture of the cells. T-cells may be isolated from the spleen or intraperitoneal cavity of animals immunized with tumor cells, but until recently it has not been possible to establish and maintain these cells for prolonged periods of time.

An important development in the investigation of T-cells has been the discovery of T-cell growth factor (TCGF), subsequently designated interleukin 2 (IL-2), which permits the continuous culture and cloning of T-lymphocytes in vitro (Braciale, T. J., Andrew, M. E., and Braciale, V. T. J. Exp. Med., 153:910–923, 1981, Gillis, S., and Smith, K. A. Nature, 268:154–156, 1977, Rosenberg, S. A., Spiess, P. J., and Schwartz, S. J. Immuno., 121:1946–1950, 1978, Ruscetti, F. W., Morgan, D. A., and Gallo, R. C. J. Immunol., 199131–138, 1977, Von Boehmer, H., Hengartner, H., Nabholz, M., Lernhardt, W., Schreier, M. H., and Haas, W. Eur. J. Immmunol., 9:592–597, (1979)).

The addition of interleukin-2 (IL-2) to activated T-cell populations allows for their continuous expansion and their establishment as long-term cell lines. This availability of cultured T-cells allows the examination of the production and regulation of lymphokines in a simplified homogeneous system.

Interferons (IFN) are a heterogeneous group of proteins that prevent replication of viruses in a host cell and thus protect against viral infections. They mediate other biological activities as well. (Stewart, W. E. 1979. The Interferon System. Springer-Verlag, New York, N.Y., Farrar, W. L., H. M. Johnson, and J. J. Farrar. J. Immunol. 126:1120, (1981)). Interferons are classified by their antigenicity into three classes: IFN-$\alpha$, IFN-$\beta$ and IFN-$\gamma$ or immune IFN (Stewart, W. E., J. E. Blalock, D. C. Burke, C. Chang, J. K. Dunnick, E. Falcoff, R. M. Friedman, G. J. Galasso, W. K. Joklik, J. T. Vilcek, J. S. Younger, and K. C. Zoon, Interferon Nomenclature, *Nature* (London) 286:110, (1980)).

IFN-$\gamma$ has been produced in vitro from peripheral blood lymphocytes in humans and spleen cell cultures in mice. (Archer, D. L., B. G. Smith, J. T. Ulrich, and H. M. Johnson. Cell. Immunol. 48:420, (1979). However, in these complex systems, the regulation of IFN-$\gamma$ production and the various activities of this lymphokine have been difficult to define (Farrar, W. L., et al. Sopra, Dinh, P. N. I. Beladi, I. Rosztoczy, and M. Toth., J. Interferon Res. 1:23, (1980)). High levels of IFN-$\alpha,\beta$ have been made available by the isolation and characterization of cell lines capable of producing these classes of IFN.

However, homogeneous T-cell clones which produce IFN-$\gamma$ and other lymphokines at significant levels are still being sought.

SUMMARY OF THE INVENTION

It has been found that the normal cytotoxic T-cell clones of the present invention are capable of producing lymphokines when stimulated with suitable mitogenic agents such as phytohemagglutinin-P (PHA-P), Conconavalin-A (Con A), polkweed mitogen (PWM), staphylococcus A (SEA), staphylococcous B (SEB) or polyinosinic-polycitidylic acid (Poly I:C), Sendai virus (SV) or Newcastle Disease virus (NDV). Thus, preferred embodiments of the present invention produce significant amounts of IFN-$\alpha$, $\beta$ when stimulated with preferred mitogenic agents Sendai Virus or Newcastle Disease Virus. Other CTLL of the present invention produce interleukin-2 when stimulated with conconavalin-A. Preferred clone CTLL-R9 produces both IFN-$\gamma$ and 2L-2 when stimulated with phorbol myristate acetate (PMA) and Con A.

The cytotoxic T-cell clones of the present invention also produce lymphokines when stimulated with antigenic agents. Thus, for example, CTLL-RP produces IFN-$\gamma$ when stimulated with RL $\delta$ 1.

The cloned cytotoxic T-cell lines of the present invention may be used to inhibit tumor growth in an individual. Thus, for example, CTLL produced from sarcoma inhibit growth of sarcoma in host animals. Likewise, CTLL of the present invention produced from radiation induced leukemia inhibit growth of similar leukemia cells.

Preferred CTLL comprise CTLL-A2, CTLL-A11, CTLL-RP, CTLL-R, CTLL-R5, CTLL-FP, CTLL-AP, CTLL-R8 CTLL-R9, CTLL-R11, CTLL-R12 and CTLL-MA10B. These preferred enbodiments have been characterized as to cell surface phenotype, histochemical and ultrastructural properties, inhibition of cytotoxicity by monosaccharides, and susceptibility to blocking by Lyt-antisera.

It is anticipated that these cytotoxic cell lines will be of significant use in the production of lymphokines for further research and for therapy of syndromes associated with disorders of the normal immune system.

Thus, these CTLL may be used to inhibit tumor growth in a mammal when injected intraperitoneally with interleukin-2 and are useful transvects for lymphokine-producing genes from other animals such as humans. The present invention also comprises a method of forming T-cell hybridomas by fusing cloned cytotoxic interleukin-2 dependent T-cell lines with immortal cell lines and establishing from these T-cell hybridomas constituent producers of various lymphokines.

DETAILED DESCRIPTION OF THE INVENTION

The following description is intended to illustrate this invention without limiting same in any manner especially with respect to substantially functional equivalents of cell lines described and claimed herein.

Abbreviations used in this paper

CTLL, cytotoxic T-lymphocyte line; IL-2, Interleukin-2; IFN, Interferon; MEM, Minimal essential medium; SV Sendai virus; NDV, Newcastle Disease virus; VSV, Vesicular Stomatitis virus; Poly I:C, Polyinosinic-Polycytidylic Acid; Con A, Concanavalin A; PHA-P, Phytohemagglutinin-P; PWM, Pokeweed Mitogen; SEA, Staphylococcus enterotoxin A; SEB, Staphylococcus enterotoxin B; GM, growth medium; CPE, cytopathic effect; PFU, Plaque forming unit, B6, C57BL/6; CB6F$_1$, (BALB/c×C57BL/6)F$_1$; PEC, peritoneal exudate cell. Deposit numbers of the Sloan Kettering Institute are designated as CTLL numbers.

Derivation of Cloned Cytotoxic T-Cell Lines

T-cell lines CTLL-AP, CTLL-A1, CTLL-A2, CTLL-A11 and CTLL-D5 were derived from the peritoneal cavity of a B6 (C57B46 obtained from Jackson Laboratories) mouse immunized with a methylcholanthrene induced sarcoma, (Meth A) of BALB/c origin. Lines CTLL-RP CTLL-R1 and CTLL-R5 were isolated from the spleens of CB6F$_1$ mice immunized with radiation induced leukemia RL ♂ 1; BALB/c origin.

Line CTLL-FP was isolated from cultures of CB6F$_1$ spleen cells immunized against BALB/c spleen cells.

For immunizations against Meth A, female B6 mice received one intradermal injection of $1 \times 10^7$ Meth A cells. Six days later, the mice were injected intraperitoneally with $5 \times 10^6$ irradiated (10,000 rads) Meth A cells. Peritoneal exudate cells (PEC) were harvested three days later. Adherent cells were removed by incubation on plastic at 37° C. three times for 30 minutes each. Direct tests, competitive inhibition tests and antibody blocking tests showed reactivity against H-2D$^d$ determinants. For immunization against RL ♂ 1 cells, six weeks after the tumor had been rejected, spleen cells were mixed with irradiated (10,000 rads) RL ♂ 1 cells (10:1 ratio) and cultured for six days. Direct tests and competitive inhibition tests showed reactivity for a unique determinant on that tumor. For immunization of F$_1$ cells against parental antigens (F$_1\alpha$P), male CB6F$_1$ spleen cells were mixed with irradiated (1,500 rads) male BALB/c spleen cells (ratio 1:1) and cultured for six days. Specificity as determined by direct tests, competitive inhibition tests and antibody blocking tests showed reactivity for parental H-2D$^d$ determinants. The cytotoxic T-cells were placed in IL-2 containing medium for expansion and cloning and established as permanent cell lines.

Human Cytotoxic T-cell Lines

Interleukin-2 dependent cytotoxic T-cell lines derived from human sources may be similarly prepared. Thus T-cells from human peripheral blood stimulated with PHA may be grown in the presence of human IL-2 containing conditioned medium. Lymphokines may be harvested from the cultured medium.

Maintenance of T-cell lines

T-cell lines were passaged by inoculating 10$^5$ cells into T-75 tissue culture flasks (Falcon #3024, Becton-Dickenson and Co., Oxnard, Calif.) containing 10 ml of GM. The cells were fed with 5 ml of GM every 3 to 4 days and passaged when the cell concentration approximated $5 \times 10^6$ per flask. All cells grew adherent to plastic.

Cloning by limiting dilution

The T-cells were seeded at $\geq 0.5$ cells/well into flat bottom plates (Falcon #3072) containing a feeder layer of irradiated (5,000 rads) syngeneic peritoneal macrophages and 200 ul of GM. After 10-14 days, the cells from positive wells were placed into 24 well Linbro plates (Flow Laboratories, Mclean, Va.) containing 2 ml of GM/well for further expansion.

Availability of Cytotoxic T-cell Lines

The cell lines disclosed in the present invention bear the designated deposit number and are deposited with Sloan-Kettering Institute, 1275 York Avenue, New York, N.Y. 10021. Preferred cell lines of the present invention are also deposited at the American Type Culture Collection, Bethesda, Md. and bear the following deposit numbers:

| CTLL # | ATCC # |
| --- | --- |
| R9 | CRL 8203 |
| RP | CRL 8201 |
| R11 | CRL 8204 |
| R12 | CRL 8205 |
| R8 | CRL 8202 |

Deposit is for the purpose of enabling disclosure only and is not intended to limit the concept of the present invention to the particular materials deposited.

Characterization of Cloned Cytotoxic T-Cell Lines

A summary of the T-cell characteristics of the various CTLL is shown in Table 1. By indirect immunofluorescence and Protein A-SRBC rosetting assays, the cytotoxic cell lines typed Lyt-2,3+. By quantitative absorption analyses low levels of Lyt-1 were detected on all cell lines tested. Effector T-cells with specificity for an H-2D$^d$ determinant, a leukemia specific or a sarcoma specific determinant were used. The effector to target cell ratio at which 50% target specific lysis was detected in a 4 hr $^{51}$Cr release assay varied from 0.1:1 to 50:1.

The Lyt antisera used in this study have been described previously (Nakayama, E., H. Shiku, E. Stockert, H. F. Oettgen, and L. J. Old, Proc. Natl. Acad. Sci. USA 76:1977, (1979)).

TABLE 1

Characterization of long term cytotoxic T-cell lines

| T-cell[a] line | Antigenic specificity | Cytotoxic[b] activity | Cell surface[c] phenotype | Source of Lymphocyte |
| --- | --- | --- | --- | --- |
| CTLL-AP | H-2D$^d$ | 5:1 | Lyt-1+,2,3+ | peritoneal cavity |
| CTLL-A1 | H-2D$^d$ | .5:1 | Lyt-1+,2,3+ | peritoneal cavity |
| CTLL-A2 | H-2D$^d$ | .1:1 | Lyt-1+,2,3+ | peritoneal cavity |
| CTLL-A11 | H-2D$^d$ | 10:1 | Lyt-1+,2,3+ | peritoneal cavity |
| CTLL-D5 | H-2D$^d$ | 20:1 | ND | peritoneal cavity |
| CTLL-RP | RL ♂ 1, unique | 40:1 | Lyt-1+,2,3+ | spleen |
| CTLL-R1 | RL ♂ 1, unique | 40:1 | Lyt-1+,2,3+ | spleen |
| CTLL-R5 | RL ♂ 1, unique | 15:1 | Lyt-1+,2,3+ | spleen |
| CTLL-FP | H-2D$^d$ | 50:1 | ND | spleen |
| CTLL-MA10B | Meth A, unique | 50:1 | Lyt-1-,2,3+ | peritoneal cavity |

[a] For Lymphoid source and strain of origin see Materials and Methods.
[b] Effector cell/target cell ratio at which 50% specific lysis is obtained during a 4 hr $^{51}$Cr release assay.
[c] Lyt-2/3 was demonstrated by protein A-SRBC Rosette Assays and indirect immunofluorescence tests. Low levels of Lyt-1 were detected by quantitative absorption analyses only.

Specificity

Direct tests, competitive inhibition tests and antibody blocking tests with clone CTLL-A11 showed reactivity for an H-2D$^d$ determinant on normal and malignant cells.

Direct tests and competitive inhibition tests show that clones CTLL-R5 and CTLL-R9 and CTLL-MA10B exhibit specificity for a unique antigen on leukemia RL ♂ 1. Clone CTLL-MA10B exhibits specificity for a highly restricted cell surface antigen on Meth A.

Cell Surface Phenotype of Cloned Cytotoxic T-Cell Lines

Analysis of the cell surface phenotypes of the three cloned cytotoxic T-cell lines by the protein A-SRBC rosette assay, and by indirect immunofluorescence tests indicated that they maintain the characteristics of the T-cell subset they initially represented (Table 1). By quantitative absorption analyses, low levels of Lyt-1 antigens were detectable on all but one of the cytotoxic T-cell clones tested. Lyt-2.2 or 3.2 determinants blocked the cytotoxicity of CTLL-R5, CTLL-A2 and CTLL-A11 while antisera directed against the Lyt-1 or Ly-5 determinants did not.

Lymphokine Production by Cloned Cytotoxic T-Cell Lines Interferon inducing agents Phytohemagglutinin-P (PHA-P) (Wellcome Research Laboratories, Beckenham, U.K.), Concanavalin A (Con A, Miles Laboratories, Elkhart, Ind.) and Pokeweed Mitogen (PWM, Sigma Chemical Co., St. Louis, Mo.) were used at a concentration of 3 ug, 5 ug and 10 ug/$10^5$ cells respectively. Staphylococcus enterotoxin A (SEA, provided by the U.S. F.D.A., Cincinnati, Ohio) and B (SEB, Sigma Chemical Co.) were used at a concentration of 0.020 ug and 0.050 ug/$10^5$ cells respectively. Polyinosinic-Polycytidylic Acid (Poly 1:C, Sigma Chemical Co.) was used at 100 ug/$10^5$ cells.

Production of IL-2

Spleen cells from CD rats ($10^6$/ml) were cultured for 2 days in Eagle's minimal essential medium (MEM) supplemented with 10% heat inactivated fetal calf serum, 2 mM L-glutamine, 1% non-essential amino acids, 100 Units penicillin/ml, 100 ug streptomycin/ml (complete MEM), $5 \times 10^{-5}$ 2-mercaptoethanol and 5 ug Con A/$10^6$ cells. After centrifugation for 10 minutes at 1000 rpm, the supernatants were sterilized by passage through a 0.20 micron Nalgene filter and stored at 4° C. The conditioned medium was used at an IL-2 activity of 20 units/ml (Growth medium: GM).

Interferon induction and assay

CTLL in complete MEM were seeded into 24 well Linbro plates (Falcon) at 105 cells/well containing various concentrations of the inducing agents described above. Conditioned medium was added at a final concentration of IL-2 of 20 units/ml except as otherwise indicated. The cells were incubated at 37° C. in a humidified 5% $CO_2$ incubator and the supernatants were tested for IFN activity after 2-4 days of culture. IFN titers were determined by a conventional cytopathic effect (CPE) inhibition assay of vesicular stomatitis virus (VSV) of L929 cells. Eighteen hours later, the cells were challenged with 5PFU/cell VSV and monitored visually for virus-induced CPE after 48 hr. A laboratory standard of murine IFN-$\alpha,\beta$ was calibrated against the National Institutes of Health standard for murine IFN-$\alpha,\beta$. IFN-$\gamma$ titers were not adjusted to the IFN-$\gamma$, reference. Antiserum to murine IFN-$\alpha,\beta$ (50,000 muIFN-$\alpha$ neutralizing units/ml and 3,000 MuIFN- neutralizing units/ml) was a generous gift of Dr. Anna Inglot (Institute of Immunology and Experimental Therapy, Wroclaw, Poland). All samples of conditioned medium were assayed for IFN-$\alpha,\beta$ and IFN-$\gamma$ levels. Various batches showed from 10-30 units of IFN-$\gamma$/ml and <10 units of IFN-$\alpha,\beta$/ml. pH-2 treated conditioned medium showed no detectable IFN-$\gamma$.

Production of IFN-$\alpha,\beta$ by CTLL in response to viral stimulation

CTLL-AP cells ($10^5$/ml) were infected with either 100 PFU of Sendai virus (SV) or Newcastle disease virus (NDV) or alternatively induced with 100 ug of Poly I:C. After 24 hr of incubation, in the presence of rat conditioned medium containing 20 units of IL-2/ml, the supernatants were assayed for antiviral activity (Table 2). Consistently high levels of IFN$\alpha,\beta$ activity were detected which was classified as IFN-$\alpha,\beta$ by the criteria listed in Table 3.

TABLE 2

Production of IFN-$\alpha,\beta$ by CTLL after viral stimulation

| T-cell line$^a$ | Units of IFN/ml inducing agents | | |
|---|---|---|---|
| | NDV | SV | Poly I:C |
| CTLL-RP | 600 | 2000 | 30 |
| CTLL-AP | 1000 | 3000 | 30 |
| CTLL-FP | 1000 | 6000 | 30 |
| CTLL-R1 | 1000 | 6000 | 30 |
| CTLL-R5 | 1000 | 6000 | 30 |
| CTLL-A1 | 1000 | 1000 | 30 |
| CTLL-A2 | 600 | 2000 | 30 |

$^a10^5$ CTLL were infected with 100 PFU of SV or NDV alternatively induced with 100 µg of Poly I:C. After 24 hr of incubation in the presence of 20 units of IL-2/ml, the supernatant fluids were assayed for antiviral activity (corrected to NIH standard).

TABLE 3

Characterization of IFN-$\alpha,\beta$ activity in supernatants of viral or mitogen stimulated CTLL

| Treatment of supernatant | Virus stimulated IFN activity | Mitogen stimulated IFN activity |
|---|---|---|
| None | + | + |
| pH 2 for 24 hr | + | − |
| Cow anti IFN-$\alpha,\beta$ antiserum | − | + |
| Trypsin 37° for 30 min. | − | − |
| RNAses | + | + |
| Incubation on guinea pig fibroblasts | + | − |

Results are expressed as positive or negative antiviral activity remaining after the indicated treatment.

Subsequently, CTLL-AP and CTLL-RP were cloned by limiting dilution at ≧0.5 cells/well. Similar patterns of IFN-$\alpha,\beta$ production were seen in response to viral stimulation. In all cases of IFN-$\alpha,\beta$ production by CTLL, SV was superior to NDV in its IFN-inducing capacity. Poly I:C did not induce any detectable IFN-$\alpha,\beta$ in the CTLL cultures.

Requirements for IL-2 during IFN-$\alpha,\beta$ production by CTLL

The effects of conditioned medium (GM) containing various levels of IL-2 on the production of IFN-$\alpha,\beta$ by CTLL was investigated. As seen in Table 4, decreasing the level of GM resulted in significantly lower levels of IFN-$\alpha,\beta$ production. At all IL-2 levels SV was better at inducing IFN production (Table 4).

Production of IFN-$\gamma$ by CTLL in response to mitogenic or antigenic stimulation CTLL were screened for both spontaneous and inducible IFN-production. $10^5$ CTLL/ml were incubated in the absence or presence of PHA-P, Con A, PWM, SEA or SEB. After 48-72 hr the supernatants were assayed for antiviral activity. Spontaneous IFN was never observed and only few of the T-cell clones produced low amounts of IFN-γ after mitogenic stimulation. Further experiments however lead to the observation that CTLL made higher levels of IFN if induced two to three days after being fed with GM.

Prior to IFN induction, CTLL-RP cells were washed three times in complete MEM and placed in conditioned medium containing the indicated concentrations of IL-2. Supernatant fluids were assayed for IFN-γ activity after 48 hr. As shown in Table 5, the amount of IFN produced increased significantly when the level of IL-2 was decreased. Priming of the T-cell cultures with 100 units of either IFN-α,β or IFN-γ for three hours had no measurable effect on IFN production. The IFN was identified as IFN-γ as summarized in Table 3.

TABLE 4

Effect of IL-2 on IFN-α,β production

| T-cell clone[a] | Units of IL-2/ml added | Units of IFN/ml inducing agents | | |
|---|---|---|---|---|
| | | NDV | SV | Poly I:C |
| CTLL-R5 | 0 | 200 | 600 | <30 |
| | 10 | 300 | 1000 | <30 |
| | 20 | 600 | 3000 | <30 |
| CTLL-A2 | 0 | 300 | 1000 | <30 |
| | 10 | 300 | 3000 | <30 |
| | 20 | 1000 | 6000 | <30 |

[a]$10^5$ CTLL were infected with 100 PFU of SV or NDV or alternatively induced with 100 μg of Poly I:C. After 24 hr incubation at the level of IL-2 indicated, supernatant fluids were assayed for antiviral activity (corrected to NIH standard).

TABLE 5

Effect of IL-2 on IFN-γ production by CTLL After mitogenic stimulation

| T-cell line[a] | Units of IL-2/ml added | Units of IFN-γ/ml[b] inducing agents | | | | |
|---|---|---|---|---|---|---|
| | | PHA-P | Con A | PWM | SEA | SEB |
| CTLL-RP | 0 | 1000 | 2000 | 1000 | 2000 | 2000 |
| | 5 | 3000 | 600 | 300 | 200 | 1000 |
| | 10 | 100 | 200 | 60 | 200 | 100 |
| | 20 | 30 | 60 | 60 | 60 | 30 |

[a]CTLL-RP were washed three times in complete MEM prior to induction.
[b]$10^5$ CTLL were induced with one of the mitogens listed above (see Materials and Methods for concentrations). After 48 hr of incubation in conditioned medium at the concentrations of IL-2, indicated supernatant fluids were assayed for antiviral activity. IFN-γ levels were not corrected to the NIH standard for IFN-α,β.

In other experiments (Table 6) the T-cell clones were washed free of conditioned medium and incubated in complete MEM during the IFN-γ production period. Forty-eight hours after the addition of the mitogen, the supernatants were harvested for the IFN-γ assay. The majority of the CTLL cells remained viable (as determined by the methylene-blue exclusion method) and could be reused for the IFN-γ production. Unstimulated CTLL incubated in Complete MEM alone failed to incorporate more than background levels of $^3$H. However, while T-cell clones were found which produced >3000 units of IFN-γ per $10^5$ cells, no correlation between IFN-production and the degree of cytotoxic activity was observed (Tables 1 and 6). An analysis of 20 other IFN-γ producing CTLL showed similar results. Only one T-cell line, CTLL-RP, produced significant levels of IFN-γ in response to incubation with the appropriate target cell antigen (Table 6). Attempts to induce IFN-γ production by incubating the CTLL with monoclonal antiserum directed to antigens on their cell surface failed to elicit any detectable antiviral activity (Table 6). Incubation of CTLL with syngeneic macrophages did not effect IFN-γ production.

TABLE 6

Production of IFN-γ by CTLL

| T-cell line[a] | Units of IFN-γ/ml Inducing agents | | | | | | |
|---|---|---|---|---|---|---|---|
| | PHA-P | Con A | PWM | SEA | SEB | Target cell[c] antigen | T-cell specific[d] antiserum |
| CTLL-RP | 1000 | 3000 | 1000 | 2000 | 1000 | 1500 | 30 |
| CTLL-AP | 10 | 200 | 100 | 100 | 10 | 30 | 30 |
| CTLL-R1 | 30 | 30 | 30 | 30 | 30 | 30 | 30 |
| CTLL-R5 | 30 | 30 | 30 | 30 | 30 | 30 | 30 |
| CTLL-A2 | 30 | 60 | 30 | 30 | 20 | 30 | 30 |
| CTLL-A11 | 20 | 100 | 20 | 20 | 20 | 30 | 30 |
| CTLL-D5 | 20 | 20 | 20 | 20 | 20 | 30 | 30 |
| CTLL-RD4[e] | 200 | 200 | 300 | ND | ND | ND | ND |
| CTLL-RB5[e] | 600 | 200 | 200 | ND | ND | ND | ND |
| CTLL-RC9[e] | 300 | 100 | 300 | ND | ND | ND | ND |
| CTLL-RE2[e] | 30 | 100 | 30 | ND | ND | ND | ND |
| CTLL-RF4[e] | 10 | 10 | 10 | ND | ND | ND | ND |

[a]CTLL were washed three times in complete MEM prior to induction.
[b]$10^5$ Washed CTLL were induced with one of the above mitogens. Supernatant fluids were assayed for antiviral activity 48 hr later.
[c]$10^6$ CTLL-RP, CTLL-R1 or CTLL-R5 were incubated with $10^5$ RL δ 1 target cells and $10^6$ CTLL-AP, CTLL-A2, CTLL-A11 or CTLL-D5 were incubated with $10^5$ Meth A cells for 48 hr.
[d]$10^5$ CTLL were incubated in Thy1.2, Lyt-1.2, Lyt-2.2 or Lyt-3.2 antiserum at a final dilution of 1:10, 1:50 or 1:100 for 48 hr.
[e]Obtained by limiting dilution of CTLL-RP cells at a concentration of ≦ 0.01 cells per well.

Production of IFN-γ and IL-2 in response to mitogenic stimulation

After stimulation with phorbol myristate acetate (PMA), also called tumor promoting agent (TPA), and Con A, clone CTLL-R9 produced both IFN-γ (1000 units/ml) and IL-2 (50 units/ml). Unstimulated CTLL-R9 cells, however, were absolutely dependent on exogenous IL-2 for continued proliferation. CTLL-R9 was tested for production of IL-3, with negative results (Table 7).

TABLE 7

Lymphokine Production by Cytotoxic T-Cell Clones[a]

| Clone | IFN-α,β | Lymphokine IFN-γ | IL-2 | IL-3 |
|---|---|---|---|---|
| CTLL-A11 | + | — | — | — |
| CTLL-R5 | + | — | — | ND |
| CTLL-R9 | ND | + | + | — |

[a]T-cell clones ($10^5$ cells/ml) were stimulated with Sendai virus, Newcastle Disease virus, PHA or PMA and Con A. The levels of lympokines were measured on days 1, 2 and 3 after induction. IFN's were measured by a CPE assay on L929 cells challenged with 10 PFU's VSV per cell. The IFN's were classified by neutralization with anti, antisera and crossreactivity on guinea pig fibroblasts. IL-2 was assayed on CTLL-A2, an IL-2 dependent cytotoxic T-cell line.

Cytotoxic T-cell Lines as Inhibitors of Tumor Growth In Vivo

Local transfer of resistance to BALB/c leukemia RL° 1 was accomplished with clone CTLL-R5 (Table 8). The growth of subcutaneously RL δ 1 injected cells in BALB/c mice was inhibited when they were mixed with CTLL-R5 cells at a ratio of 1:10. By contrast, another BALB/c leukemia RV1 (radiation virus induced) was not inhibited when mixed with CTLL-R5 cells. These results are compatible with the unique specificity of CTLL-R5 in in vitro tests. Systemic transfer of resistance to tumor allografts was investigated with CTLL-A11 which had been shown to be specific for H-2D[d] determinants on BALB/c sarcoma Meth A and other cells (Table 9). While intraperitoneal injection of CTLL-A11 alone, 2 hours after subcutaneous injection of Meth A tumor cells into B6 mice, did not inhibit tumor growth, injection of CTLL-A11 with IL-2 (but not Il-2 alone) was inhibitory.

TABLE 8

Local Transfer of Resistance to Syngeneic
Tumor Grafts with Cloned Cytotoxic T-Cells

| Injected tumor | CTLL-R5 admixed | Number of mice with tumors/total number | | |
|---|---|---|---|---|
| | | Day 7 | Day 10 | Day 14 |
| BALB/c RL ♂ 1 | − | 2/9 | 6/9 | 8/9 |
| BALB/c RL ♂ 1 | + | 0/9 | 0/9 | 3/9 |
| BALB/c RV1 | − | 0/5 | 3/5 | 5/5 |
| BALB/c RV1 | + | 0/5 | 3/5 | 5/5 |

$10^5$ tumor cells were mixed with $10^6$ CTLL-R5 (washed free of IL-2) and injected intradermally into BALB/c recipients.

TABLE 9

Systemic Transfer of Resistance to Tumor
Allografts with Cloned Cytotoxic T-cells
Combined with IL-2

| BALB/c sarcoma Meth A | CTLL-A11 IP | IL-2 IP | Tumor diameter (mm) on | | |
|---|---|---|---|---|---|
| | | | Day 7 | Day 10 | Day 14 |
| + | − | − | 53 | 49 | 21 |
| + | − | + | 50 | 54 | 26 |
| + | + | − | 49 | 56 | 28 |
| + | + | + | 27 | 31 | 17 |

$10^7$ Meth A cells were injected subcutaneously into B6 mice. $5 \times 10^6$ CTLL-A11 and 100 units of IL-2 (DEAE-Sephadex purified IL-2 from Con A stimulated rat spleen cells provided by Collaborative Research, Waltham, MA) were injected intraperitoneally two hours later as indicated.

Cytotoxic T-Cell Lines as Transvects for Gene Transplants

The ability of the IL-2 dependent cytotoxic T-cell lines of the present invention to grow over prolonged periods of time in vitro makes them suitable for use as transvects for gene transplants from the same or other species. The ability of these CTLL to adhere to plastic increases their usefulness in this regard. Thus, for example, a murine or human gene which produces a lymphokine such as interferon or interleukin-2 may be transplanted into a CTLL of the present invention by methods well known in the art. The gene thus transplanted will express the lymphokine which may be harvested in significant amounts from the growing culture medium.

Lymphokine-Producing T-Cell Hybridomas from CTLL

Interleukin-2 dependent CTLL of the present invention may be fused with an immortal cell line to form hybridomas which are constituent producers of various lymphokines. These lymphokine-producing hybridomas may be formed from CTLL by fusing by methods known in the art, for example, the Köhler-Milstein procedure, with an immortal T-cell line from $B_{VR}$-thymoma, preferrably BW5147. Fusion with human T-cell lines is also possible with the cell lines of the present invention. The interleukin-2 dependent cytotoxic T-cell lines of either human or murine origin may be used to form lymphokine-producing T-cell hybridomas.

SUMMARY

Interleukin-2 (IL-2) dependent cytotoxic T-cell lines (CTLL) reactive for an H-2D$^d$ antigen or a leukemia specific antigen may be stimulated to produce the $\alpha,\beta$ and $\gamma$ types of interferon (IFN) and IL-2. After infection with Sendai virus (SV) or Newcastle Disease virus (NDV), the investigated CTLL produced moderate to high levels of IFN-$\alpha,\beta$. The production of IFN-$\alpha,\beta$ decreased when the level of IL-2 present during the induction period was lowered. The production of IFN-$\gamma$ showed heterogeneity: Only particular CTLL synthesized detectable levels (>10 units/ml) and only particular mitogens were effective inducers. In contrast to the production of IFN$\alpha,\beta$, IFN-$\gamma$ levels were dramatically increased at lower IL-2 concentrations. Incubation of the CTLL with their specific target antigen elicited significant IFN-$\gamma$ production in only one of seven CTLL. Stimulation of the CTLL with antibodies directed to antigens on their surface failed to induce IFN-$\gamma$ production. The induced IFN's were classified by (1) stability to pH2 treatment, (2) neutralization by IFN-$\gamma$, antiserum, (3) crossreactivity on guinea pig fibroblasts, (4) sensitivity to trypsinization and (5) stability to RNase treatment. The results indicate that some CTLL can produce IFN-$\alpha,\beta$, IFN-$\gamma$ and IL-2 after the appropriate stimulation. The availability of CTLL now affords us the opportunity to study lymphokine production at the clonal level.

I claim:

1. A method of stimulating production of the lymphokines $\alpha$-interferon and $\beta$-interferon by interleukin-2 dependent cytotoxic cultured T-cell lines comprising administering to a T-cell line selected from the group consisting of T-cell lines CTLL-RP (CRL 8201), CTLL-R8 (CRL 8202), CTLL-R9 (CRL 8203), CTLL-R11 (CRL 8204), and CTLL-R12 (CRL 8205), an amount of an antigen selected from the group consisting of Newcastle Disease Virus and Sendai Virus sufficient to cause stimulation of production of said lymphokines.

2. A method as in claim 1, wherein said T-cell line is cytotoxic cultured T-cell line CTLL-RP (CRL-8201).

3. A method of stimulating production of $\gamma$-interferon by interleukin-2 dependent cytotoxic T-cell lines which also produce $\alpha$- and $\beta$-interferon comprising administering to a T-cell line selected from the group consisting of T-cell lines CTLL-RP (CRL 8201), CTLL-R8 (CRL 8202), CTLL-R9 (CRL 8203), CTLL-R11 (CRL 8204) and CTLL-12 (CRL 8205), an amount of a mitogenic or antigenic stimulant selected from the group consisting of Phytohemagglutinin-P, Concanavalin A, Pokeweed mitogen, Staphylococcus enterotoxic A, Staphylococcus enterotoxin B, RL ♂ 1 antigen, and Meth A antigen sufficient to stimulate production of $\gamma$-interferon.

4. A method as in claim 1, wherein said T-cell line is cytotoxic cultured T-cell line CTLL-RP (CRL 8201).

5. A method as in claim 1, wherein said T-cell line is cytotoxic cultured T-cell line CTLL-RP (CRL 8201), and said mitogenic or antigenic agent is RL ♂ 1 antigen.

6. A biologically pure culture of interleukin-2 dependent cytoxic cultured T-cell lines selected from the group consisting of CTLL-RP (CRL 8201), CTLL-R8 (CRL 8202), CTLL-R9 (CRL 8203), CTLL-R11 (CRL 8204), and CTLL-R12 (CRL 8205), said cell lines producing $\alpha$-interferon and $\beta$-interferon when an amount of an inducing agent selected from the group consisting of Newcastle Disease Virus and Sendai Virus sufficient to cause stimulation of said product is administered thereto, and producing $\gamma$-interferon when an amount of mitogenic or antigenic stimulant selected from the group consisting of Phytohemagglutinin-P, Concanavalin A, Pokeweed mitogen, Staphylococcus enterotoxin A, Staphylococcus enterotoxin B, RL ♂ 1 antigen, and Meth A antigen sufficient to cause stimulation is administered thereto.

7. Interleukin-2 dependent cytotoxic cultured T-cell lines of claim 5, wherein said cell lines are specific for the H-2D$^d$ determinant on normal and malignant cells.

8. Interleukin-2 dependent cytotoxic cultured T-cell lines of claim 5, wherein said cell lines are specific for RL ♂ 1 antigen.

9. A method of stimulating production of both γ-interferon and interleukin-2 dependent cytotoxic cultured T-cell line CTLL-R9 (CRL 8203) which also produces α, and β-interferon comprising administering to said cell lines amounts of pharbol myristate acetate and concanvalin A sufficient to stimulate production of both γ-interferon and interleukin-2.

* * * * *